(12) United States Patent
Marx et al.

(10) Patent No.: US 9,249,170 B2
(45) Date of Patent: Feb. 2, 2016

(54) CYCLIC ALKYL AMINO CARBENE (CAAC) RUTHENIUM COMPLEXES AS IMPROVED CATALYSTS FOR ETHENOLYSIS REACTIONS

(71) Applicants: Vanessa M. Marx, Pasadena, CA (US); Mohand-Ameziane Melaimi, San Diego, CA (US); Scott C. Virgil, Pasadena, CA (US); Benjamin K. Keitz, Pasadena, CA (US); Robert H. Grubbs, South Pasadena, CA (US); Guy Bertrand, Solana Beach, CA (US)

(72) Inventors: Vanessa M. Marx, Pasadena, CA (US); Mohand-Ameziane Melaimi, San Diego, CA (US); Scott C. Virgil, Pasadena, CA (US); Benjamin K. Keitz, Pasadena, CA (US); Robert H. Grubbs, South Pasadena, CA (US); Guy Bertrand, Solana Beach, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/249,704

(22) Filed: Apr. 10, 2014

(65) Prior Publication Data

US 2014/0309433 A1 Oct. 16, 2014

Related U.S. Application Data

(60) Provisional application No. 61/810,795, filed on Apr. 11, 2013.

(51) Int. Cl.
| | | |
|---|---|---|
| C07D 405/04 | (2006.01) | |
| C07F 15/00 | (2006.01) | |
| C07C 1/207 | (2006.01) | |
| C07C 6/04 | (2006.01) | |

(52) U.S. Cl.
CPC ............ C07F 15/0046 (2013.01); C07C 1/2078 (2013.01); C07C 6/04 (2013.01); C07D 405/04 (2013.01); C07C 2531/22 (2013.01)

(58) Field of Classification Search
CPC ...................................................... C07D 405/05

USPC .......................................................... 548/577
See application file for complete search history.

(56) References Cited

U.S. PATENT DOCUMENTS

| | | | |
|---|---|---|---|
| 7,312,331 B2 | 12/2007 | Bertrand et al. | |
| 8,063,232 B2 | 11/2011 | Hagadorn et al. | |
| 8,067,610 B2 | 11/2011 | Schrodi | |
| 8,329,921 B2 | 12/2012 | Hagadorn et al. | |
| 8,501,973 B2 | 8/2013 | Schrodi et al. | |
| 2010/0022789 A1* | 1/2010 | Mignani et al. | 554/161 |
| 2013/0231499 A1 | 9/2013 | Grubbs et al. | |

FOREIGN PATENT DOCUMENTS

| | | |
|---|---|---|
| FR | 2934178 A1 | 1/2010 |
| FR | 2947189 A1 | 12/2010 |

OTHER PUBLICATIONS

Mignani, et al. Document No. 152:215450, retrieved from CAPLUS; 20100129.*
Marx et al., "Asymmetric cyclic alkyl amino carbene (CAAC) ruthenium complexes as improved catalysts for ethenolysis", Abstracts of Papers, 245th ACS National Meeting & Exposition, New Orleans, LA, United States, Apr. 7-11, 2013 (2013), INOR-1195. Publisher: (American Chemical Society, Washington, D.C.) CODEN:69QTVP.
Anderson et al., "Synthesis and Reactivity of Olefin Metathesis Catalysts Bearing Cyclic(Alkyl)(Amino)Carbenes," Angew. Chem. Int. Ed., 46:7262-7265 (2007).
Nickel et al., "A Highly Efficent Olefin Metathesis Process for the Synthesis of Terminal Alkenes from Fatty Acid Esters," Top Catal., 55:518-523 (2012).
Schrodi et al., "Ruthenium Olefin Metathesis Catalysts for the Ethenolysis of Renewable Feedstocks," Clean, 36(8):669-673 (2008).
Zhang et al., "Ruthenium-catalyzed olefin metathesis accelerated by the steric effect of the backbone substituent in cyclic (alkyl)(amino) carbenes," Chem. Commun., 49:9491-9493 (2013).

* cited by examiner

*Primary Examiner* — Shawquia Jackson
(74) *Attorney, Agent, or Firm* — David P. Halstead; Foley Hoag LLP

(57) ABSTRACT

Described herein are compounds and methods of catalyzing ethenolysis reactions, optionally on an industrial scale. In certain embodiments, the catalysts bear cyclic alkyl amino carbene (CAAC) ligands with an ortho substituent, such as a methyl substituent, on an N-aryl ring. When used to catalyze ethenolysis reactions, certain such compounds produce a turnover number greater than 50,000.

21 Claims, 3 Drawing Sheets

C
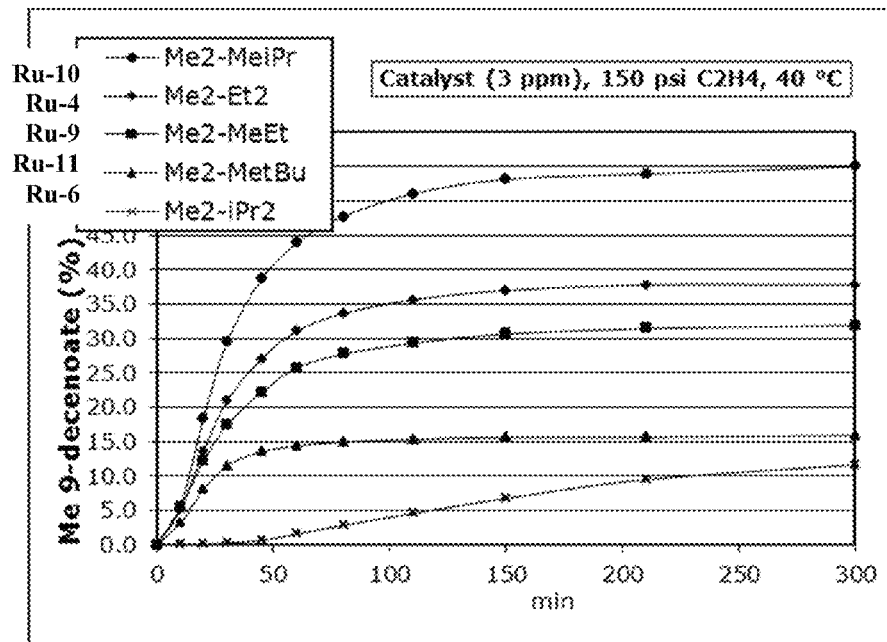
| | Me2 | Me2 | Me2 | Me2 | Me2 |
| --- | --- | --- | --- | --- | --- |
| | MeiPr | Et2 | MeEt | MetB | iPr2 |
| 0 | 0.0 | 0.0 | 0.0 | 0.0 | 0.0 |
| 10 | 5.6 | 5.1 | 5.4 | 3.1 | 0.0 |
| 20 | 18.4 | 13.6 | 12.2 | 8.1 | 0.1 |
| 30 | 29.5 | 20.9 | 17.4 | 11.5 | 0.3 |
| 45 | 38.7 | 27.1 | 22.1 | 13.5 | 0.6 |
| 60 | 43.9 | 31.1 | 25.7 | 14.4 | 1.6 |
| 80 | 47.7 | 33.6 | 27.7 | 14.9 | 2.8 |
| 110 | 51.0 | 35.6 | 29.3 | 15.3 | 4.6 |
| 150 | 53.2 | 37.0 | 30.6 | 15.6 | 6.7 |
| 210 | 53.9 | 37.8 | 31.4 | 15.6 | 9.5 |
| 300 | 55.0 | 37.8 | 31.9 | 15.9 | 11.6 |

CYCLIC ALKYL AMINO CARBENE (CAAC) RUTHENIUM COMPLEXES AS IMPROVED CATALYSTS FOR ETHENOLYSIS REACTIONS

CROSS-REFERENCE TO RELATED APPLICATIONS

The present application claims the benefit of U.S. Provisional Application No. 61/810,795, filed on Apr. 11, 2013, which is incorporated herein by reference in its entirety.

GOVERNMENT SUPPORT

This invention was made with Government support under Grant Nos. GM031332 and GM068825, both awarded by the National Institutes of Health and Grant No. CHE1048404 awarded by the National Science Foundation. The government has certain rights in the invention.

BACKGROUND

The transformation of chemical feedstocks into industrially relevant small molecules has been a long-standing challenge that has received a significant resurgence of interest in the chemical sciences. This will enable the inexpensive preparation of a wide variety of useful products ranging from fuels to pharmaceuticals. Many inexpensive, renewable or bio-based materials, such as fatty acids originating from seed oils and their derivatives, contain at least one unit of unsaturation, providing a synthetic handle for derivatization by olefin metathesis catalysts. The production of linear alpha olefins (LAOs) from the ethenolysis of seed oil derivatives has been demonstrated. For example, catalyst Ru-4

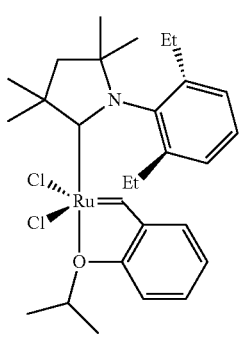
Ru-4

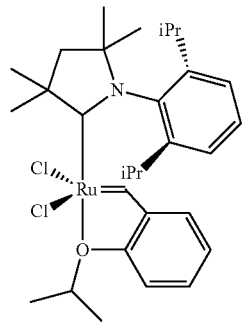
Ru-6 provided ethenolysis products in 35% yield (83% selectivity) using catalyst loadings of 10 ppm (turnover number (TON) =35,000), for the ethenolysis of methyl oleate (1) to 1-decene (2) and methyl-10-undecenoate (3) (Scheme 1):

Scheme 1.

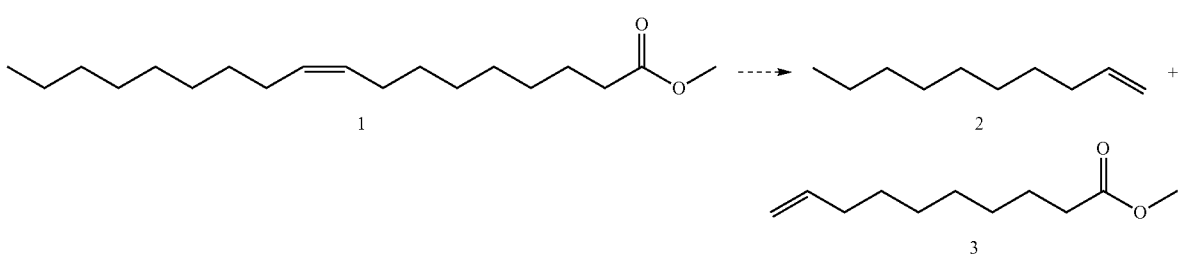

However, high catalyst loadings are needed in order to achieve good selectivity for terminal olefins, making this particular system cost-prohibitive on an industrial scale.

There exists a need for systems capable of catalyzing ethenolysis reactions with high activity and selectivity on an industrial scale.

SUMMARY OF THE INVENTION

In certain embodiments, the invention relates to a compound, wherein the compound is
(A) a compound of Formula I:

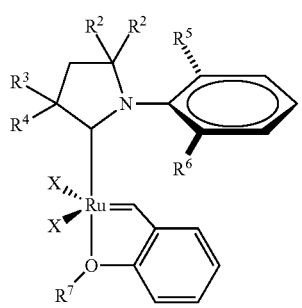
Formula I wherein, independently for each occurrence,

X is, independently for each occurrence, a monovalent ligand, such as alkoxy or (preferably) halo, most preferably chloro;

$R^2$ is, independently for each occurrence, alkyl, preferably methyl;

$R^3$ is alkyl, preferably methyl;

$R^4$ is alkyl, aryl, heteroaryl, aralkyl, or heteroaralkyl;

or $R^3$ and $R^4$, taken together with the carbon atom to which they are attached, form a five-, six-, or ten-membered cycloalkyl or heterocyclyl ring;

$R^5$ is alkyl;

$R^6$ is H or alkyl (preferably methyl or ethyl, most preferably methyl), provided that (i) $R^5$ and $R^6$ are not the same, and (ii) $R^6$ has fewer atoms than $R^5$; and $R^7$ is alkyl, preferably a secondary or tertiary alkyl, most preferably 2-propyl;

(B) a compound of Formula II:

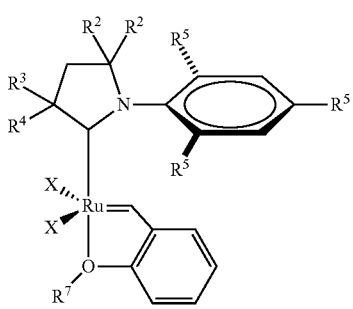

Formula II wherein, independently for each occurrence,

X is, independently for each occurrence, a monovalent ligand, such as alkoxy or (preferably) halo, most preferably chloro;

$R^2$ is, independently for each occurrence, alkyl, preferably methyl;

$R^3$ is alkyl, preferably methyl;

$R^4$ is alkyl, aryl, heteroaryl, aralkyl, or heteroaralkyl;

or $R^3$ and $R^4$, taken together with the carbon atom to which they are attached, form a five-, six-, or ten-membered cycloalkyl or heterocyclyl ring;

$R^5$ is, independently for each occurrence, alkyl, preferably methyl; and $R^7$ is alkyl, preferably a secondary or tertiary alkyl, most preferably 2-propyl;

(C) a compound of Formula III:

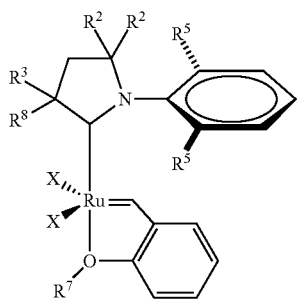

Formula III wherein, independently for each occurrence,

X is, independently for each occurrence, a monovalent ligand, such as alkoxy or (preferably) halo, most preferably chloro;

$R^2$ is alkyl, preferably methyl;

$R^3$ is alkyl, preferably methyl;

$R^5$ is, independently for each occurrence, alkyl, preferably methyl or ethyl;

$R^7$ is alkyl, preferably a secondary or tertiary alkyl, most preferably 2-propyl; and $R^8$ is aryl or heteroaryl, preferably substituted or unsubstituted phenyl, most preferably unsubstituted phenyl; or (D) a compound of Formula IV:

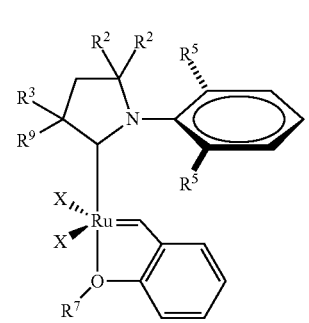

Formula IV wherein, independently for each occurrence,

X is, independently for each occurrence, a monovalent ligand, such as alkoxy or (preferably) halo, most preferably chloro;

$R^2$ is alkyl, preferably methyl;

$R^3$ is alkyl, preferably methyl;

$R^5$ is, independently for each occurrence, alkyl, preferably methyl or ethyl;

$R^7$ is alkyl, preferably a secondary or tertiary alkyl, most preferably 2-propyl;

$R^9$ is $C_2$-$C_6$ alkyl, preferably n-propyl;

or $R^3$ and $R^9$, taken together with the carbon atom to which they are attached, form a five-, or ten-membered cycloalkyl or heterocyclyl ring.

In other embodiments, the invention relates to a compound selected from:

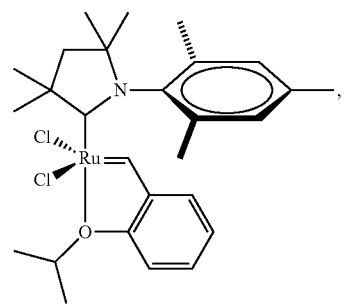

,

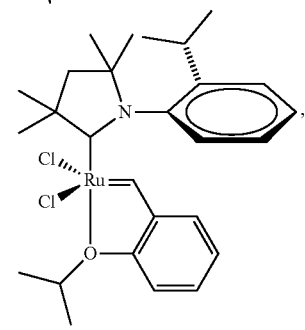

,

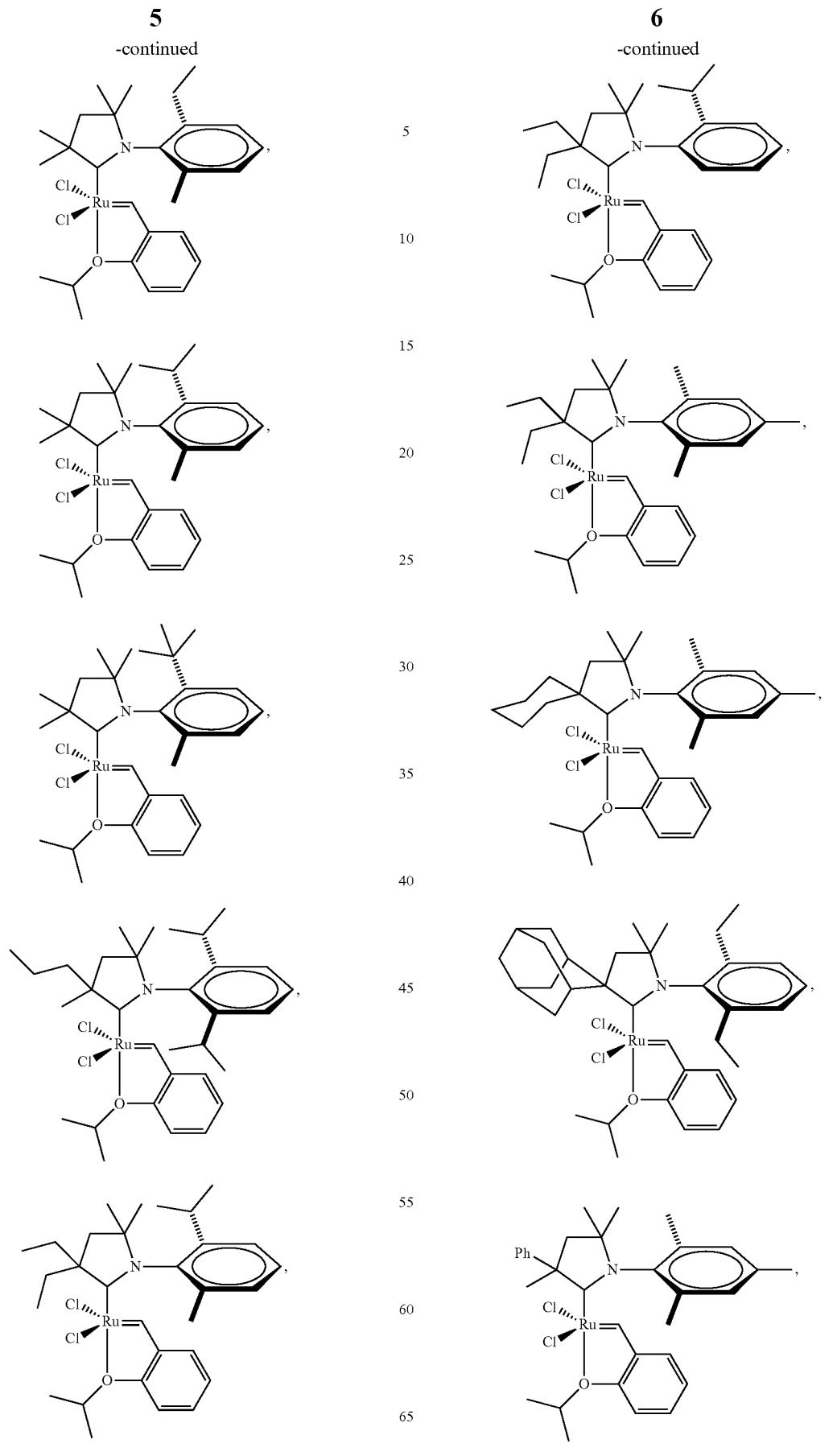

-continued

-continued

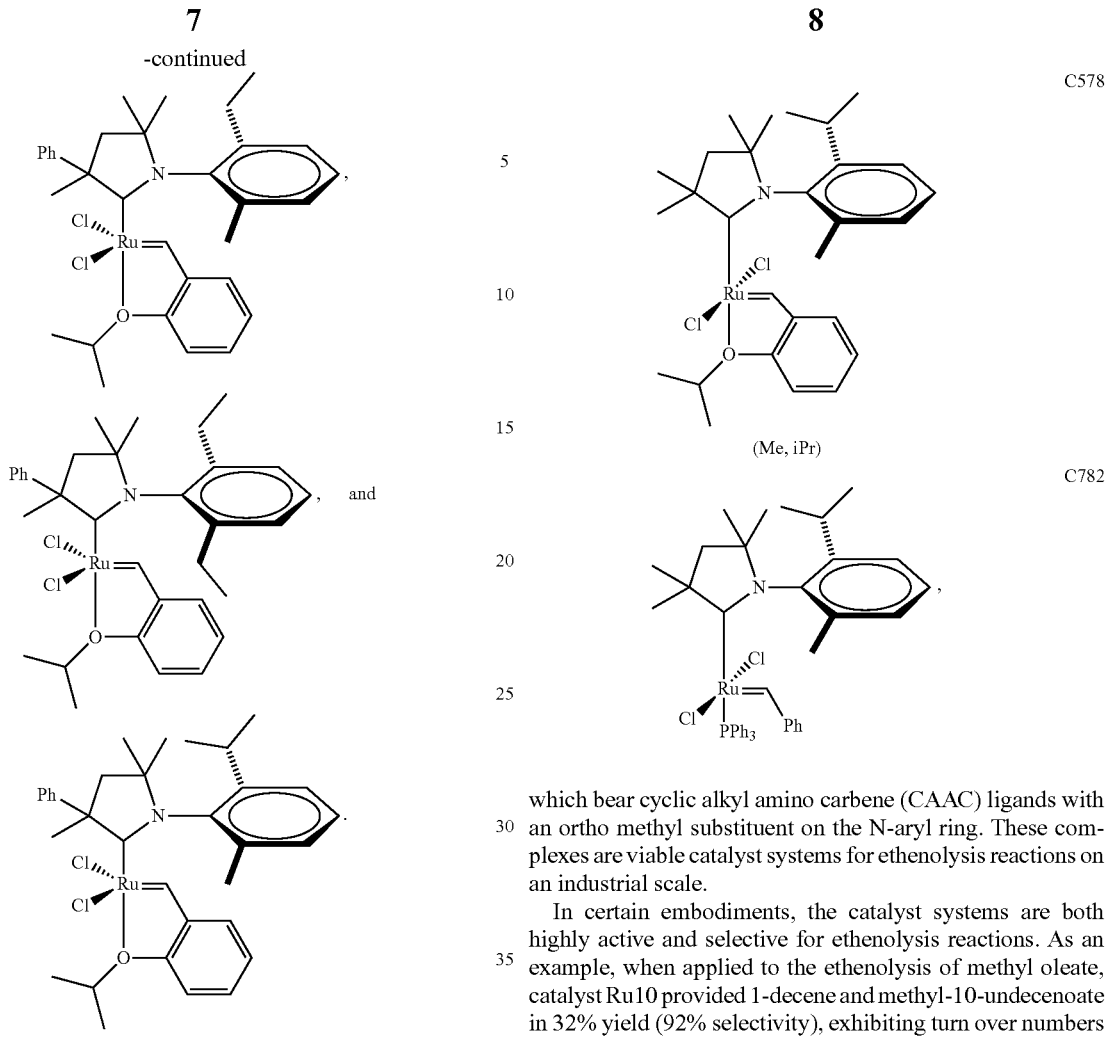

(Me, iPr)

C782 which bear cyclic alkyl amino carbene (CAAC) ligands with an ortho methyl substituent on the N-aryl ring. These complexes are viable catalyst systems for ethenolysis reactions on an industrial scale.

In certain embodiments, the catalyst systems are both highly active and selective for ethenolysis reactions. As an example, when applied to the ethenolysis of methyl oleate, catalyst Ru10 provided 1-decene and methyl-10-undecenoate in 32% yield (92% selectivity), exhibiting turn over numbers (TON) of 106,000. In one embodiment, the catalysts are used in the transformation of seed oil derivatives into commodity materials on an industrial scale.

Exemplary Compounds

In certain embodiments, the invention relates to a compound, wherein the compound is (A) a compound of Formula I:

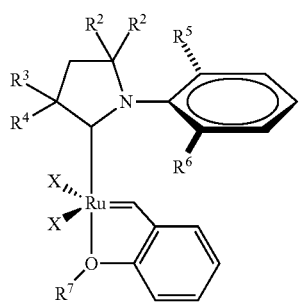

Formula I wherein, independently for each occurrence,

X is, independently for each occurrence, a monovalent ligand, such as alkoxy or (preferably) halo, most preferably chloro;

$R^2$ is, independently for each occurrence, alkyl;

$R^3$ is alkyl, preferably methyl;

$R^4$ is alkyl, aryl, heteroaryl, aralkyl, or heteroaralkyl;

In still other embodiments, the invention relates to a method of producing an olefin product comprising:

providing an olefinic substrate;

providing an alpha olefin;

contacting the olefinic substrate with the alpha olefin in the presence of any one of the compounds described herein under reaction conditions effective to allow a metathesis reaction to occur, thereby producing the olefin product.

DETAILED DESCRIPTION OF THE INVENTION

Overview

Figure 1:
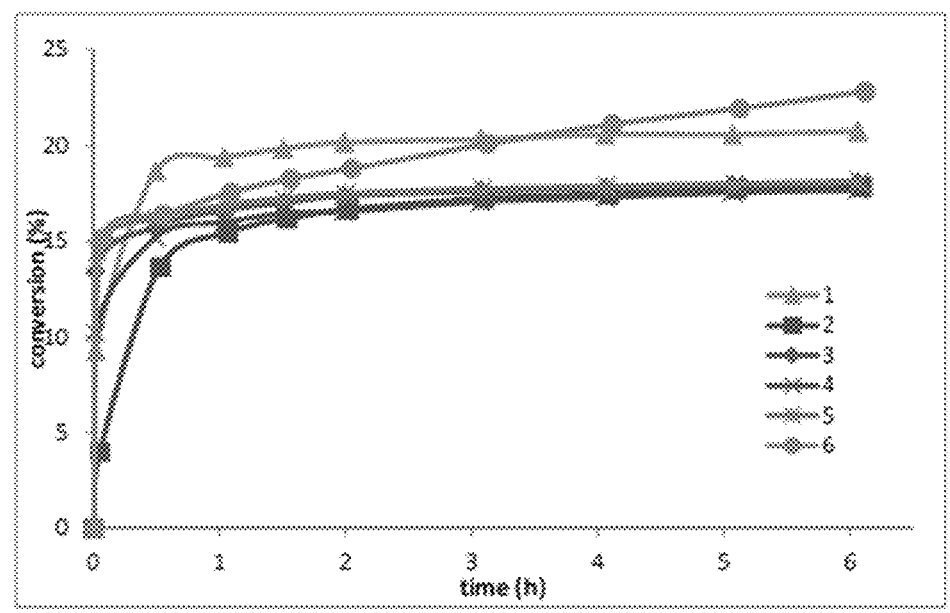
FIG. 1 depicts the evolution of conversion as a function of reaction time in the ethenolysis of 1-hexene catalyzed by various compounds of the invention.

In one aspect, the invention relates to ruthenium complexes, such as C578 (Me, iPr) (i.e., Ru10) or C782 or $R^3$ and $R^4$, taken together with the carbon atom to which they are attached, form a five-, six-, or ten-membered cycloalkyl or heterocyclyl ring;

$R^5$ is alkyl;

$R^6$ is H or alkyl (preferably methyl or ethyl, most preferably methyl), provided that (i) $R^5$ and $R^6$ are not the same, and (ii) $R^6$ has fewer atoms than $R^5$; and $R^7$ is alkyl, preferably a secondary or tertiary alkyl, most preferably 2-propyl;

(B) a compound of Formula II:

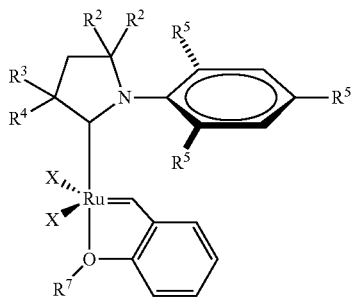

Formula II wherein, independently for each occurrence,

X is, independently for each occurrence, a monovalent ligand, such as alkoxy or (preferably) halo, most preferably chloro;

$R^2$ is, independently for each occurrence, alkyl, preferably methyl;

$R^3$ is alkyl, preferably methyl;

$R^4$ is alkyl, aryl, heteroaryl, aralkyl, or heteroaralkyl;

or $R^3$ and $R^4$, taken together with the carbon atom to which they are attached, form a five-, six-, or ten-membered cycloalkyl or heterocyclyl ring;

$R^5$ is, independently for each occurrence, alkyl, preferably methyl; and $R^7$ is alkyl, preferably a secondary or tertiary alkyl, most preferably 2-propyl;

(C) a compound of Formula III:

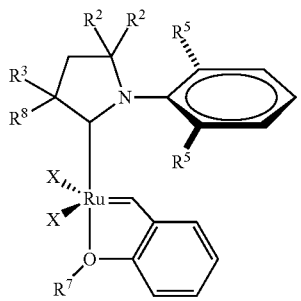

Formula III wherein, independently for each occurrence,

X is, independently for each occurrence, a monovalent ligand, such as alkoxy or (preferably) halo, most preferably chloro;

$R^2$ is alkyl, preferably methyl;

$R^3$ is alkyl, preferably methyl;

$R^5$ is, independently for each occurrence, alkyl, preferably methyl or ethyl;

$R^7$ is alkyl, preferably a secondary or tertiary alkyl, most preferably 2-propyl; and $R^8$ is aryl or heteroaryl, preferably substituted or unsubstituted phenyl, most preferably unsubstituted phenyl; or (D) a compound of Formula IV:

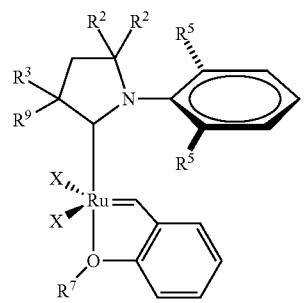

Formula IV wherein, independently for each occurrence,

X is, independently for each occurrence, a monovalent ligand, such as alkoxy or (preferably) halo, most preferably chloro;

$R^2$ is alkyl, preferably methyl;

$R^3$ is alkyl, preferably methyl;

$R^5$ is, independently for each occurrence, alkyl, preferably methyl or ethyl;

$R^7$ is alkyl, preferably a secondary or tertiary alkyl, most preferably 2-propyl;

$R^9$ is $C_2$-$C_6$ alkyl, preferably n-propyl;

or $R^3$ and $R^9$, taken together with the carbon atom to which they are attached, form a five-, or ten-membered cycloalkyl or heterocyclyl ring.

In certain embodiments, the invention relates to any one of the compounds mentioned herein, wherein X is halo, such as chloro.

In certain embodiments, the invention relates to any one of the compounds mentioned herein, wherein $R^2$ is lower alkyl, such as methyl.

In certain embodiments, the invention relates to any one of the compounds mentioned herein, wherein $R^3$ is lower alkyl.

In certain embodiments, the invention relates to any one of the compounds mentioned herein, wherein $R^3$ is methyl, or, in other embodiments, ethyl.

In certain embodiments, the invention relates to any one of the compounds mentioned herein, wherein $R^4$ is lower alkyl.

In certain embodiments, the invention relates to any one of the compounds mentioned herein, wherein $R^4$ is methyl, or, in other embodiments, ethyl.

In certain embodiments, the invention relates to any one of the compounds mentioned herein, wherein $R^4$ is aryl, such as phenyl.

In certain embodiments, the invention relates to any one of the compounds mentioned herein, wherein $R^3$ and $R^4$, taken together with the carbon atom to which they are attached, form a cyclohexyl ring.

In certain embodiments, the invention relates to any one of the compounds mentioned herein, wherein $R^5$ is lower alkyl, such as methyl, ethyl, propyl, or butyl. In certain embodiments, the invention relates to any one of the compounds mentioned herein, wherein $R^5$ is methyl. In certain embodiments, the invention relates to any one of the compounds mentioned herein, wherein $R^5$ is ethyl. In certain embodiments, the invention relates to any one of the compounds mentioned herein, wherein $R^5$ is iso-propyl. In certain embodiments, the invention relates to any one of the compounds mentioned herein, wherein $R^5$ is tert-butyl.

In certain embodiments, the invention relates to any one of the compounds mentioned herein, wherein $R^6$ is H or lower alkyl. In certain embodiments, the invention relates to any one of the compounds mentioned herein, wherein $R^6$ is H. In certain embodiments, the invention relates to any one of the compounds mentioned herein, wherein $R^6$ is methyl.

In certain embodiments, the invention relates to any one of the compounds mentioned herein, wherein $R^7$ is lower alkyl. In certain embodiments, the invention relates to any one of the compounds mentioned herein, wherein $R^7$ is propyl, such as iso-propyl.

In certain embodiments, the invention relates to any one of the compounds mentioned herein, wherein $R^8$ is aryl, such as phenyl.

In certain embodiments, the invention relates to any one of the compounds mentioned herein, wherein $R^9$ is n-propyl.

In certain embodiments, the invention relates to any one of the compounds mentioned herein, wherein $R^3$ and $R^9$, taken together with the carbon atom to which they are attached, form an adamantyl ring.

In certain embodiments, the invention relates to any one of the compounds mentioned herein, provided the compound is not

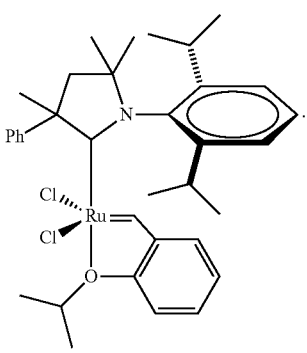

In other embodiments, the invention relates to a compound selected from:

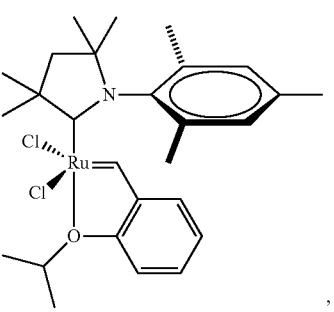

,

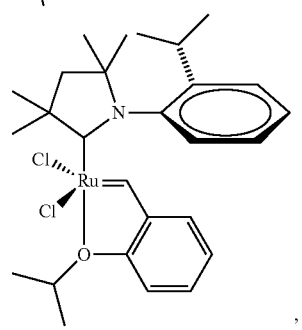

,

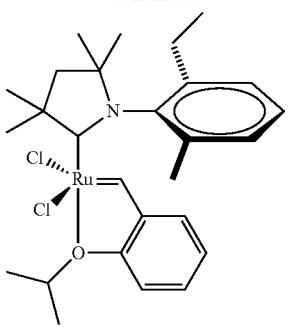

,

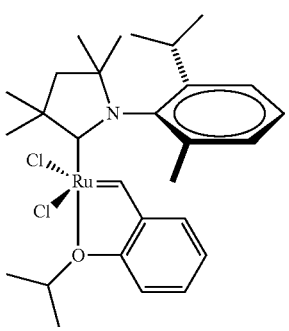

,

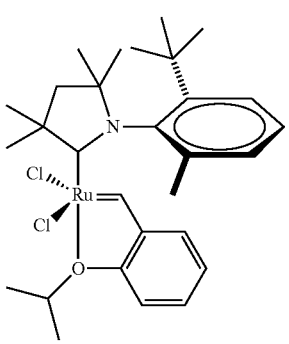

,

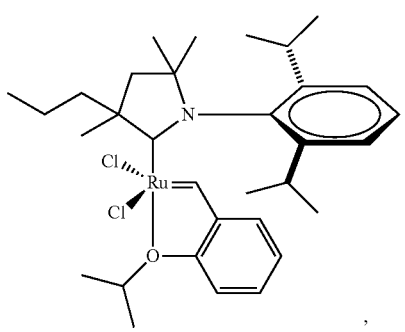

,

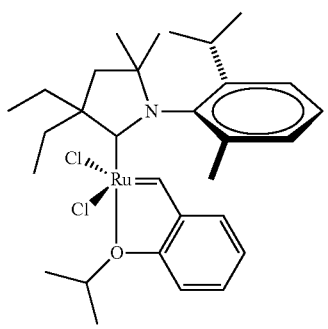

,

-continued

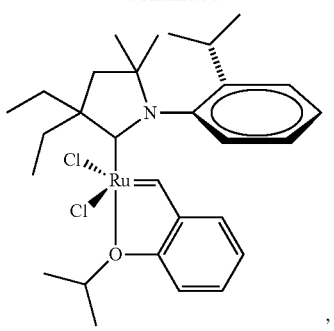

,

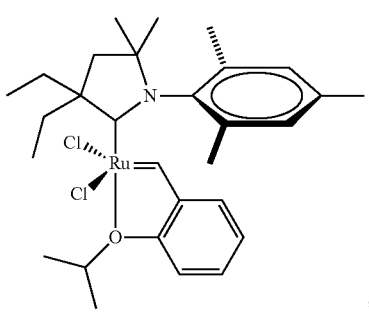

,

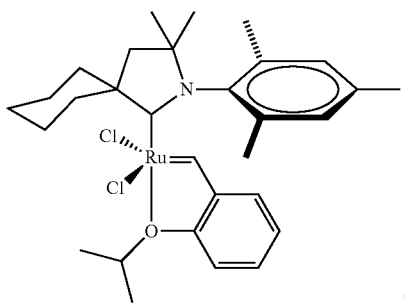

,

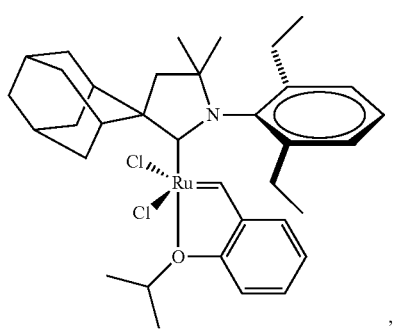

,

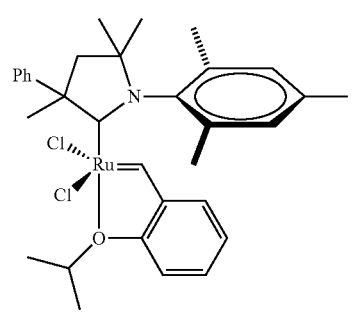

,

-continued

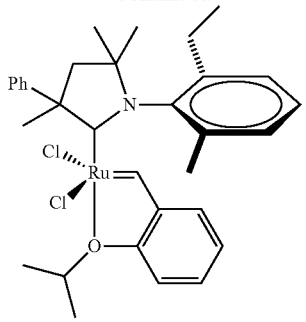

,

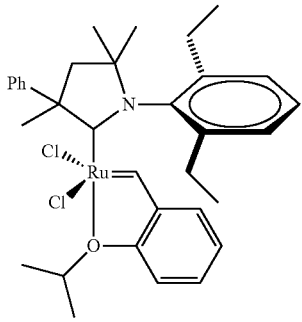

,

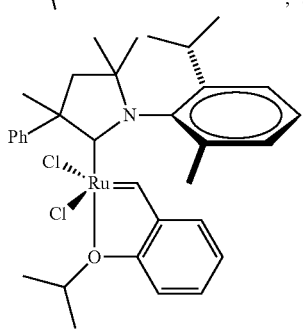

, and

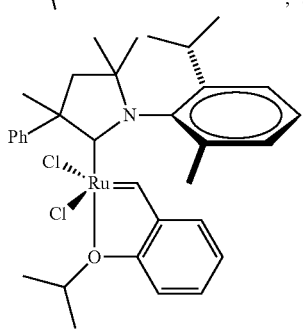

.

Exemplary Methods

In certain embodiments, the invention relates to a method of producing an olefin product comprising:
providing an olefinic substrate;
providing an alpha olefin;
contacting the olefinic substrate with the alpha olefin in the presence of any one of the compounds described herein (i.e., catalysts of the invention) under reaction conditions effective to allow a metathesis reaction to occur, thereby producing the olefin product.

In certain embodiments, the invention relates to any one of the methods described herein, wherein the olefin product is a terminal olefin product.

In certain embodiments, the olefinic substrate comprises at least one internal olefin, and may have 2 or more internal olefins. For example, the olefinic substrate may comprise in the range of 2 to about 15, 2 to about 10, or 2 to about 5 internal olefins. By "internal olefin" is meant an olefin wherein each of the olefinic carbons is substituted by at least one non-hydrogen substituent preferably a hydrocarbyl substituent. The non-hydrogen substituents are selected from unsubstituted hydrocarbyl, substituted hydrocarbyl, and functional groups. The internal olefin is therefore at least disubstituted, and may further include additional non-hydrogen substituents such that the internal olefin is tri- or tetra-substituted. Each of the substituents on the internal olefinic carbons may be further substituted as described herein. The internal olefin may be in the Z- or E-configuration. When the olefinic substrate comprises a plurality of internal olefins, the olefinic substrate may comprise a mixture of internal olefins (varying in stereochemistry and/or substituent identity), or may comprise a plurality of internal olefins.

The olefinic substrate may be a single compound or a mixture of compounds. The olefinic substrate may be hydrophobic or hydrophilic, although in a preferred embodiment, the olefinic substrate is hydrophobic.

In certain embodiments, the olefinic substrate is a cyclic olefin.

As another example, the olefinic substrate is an ester of glycerol (a "glyceride"). In a preferred embodiment, the olefinic substrate comprises glycerol esterified with 1, 2, or 3 fatty acids, such that the olefinic substrate is a monoacylglycerol, diacylglycerol, or triacylglycerol (i.e., a monoglyceride, diglyceride, or triglyceride, respectively), or a mixture thereof. Each fatty acid-derived fragment of the olefinic substrate may independently be saturated, monounsaturated, or polyunsaturated, and may furthermore derive (or be derivable) from naturally-occurring fatty acids or from synthetic fatty acids. For example, the olefinic substrate may comprise glycerol esterified with one, two, or three fatty acids that are independently selected from $CH_3(CH_2)_nCOOH$, where n is 2, 3, 4, 5, 6, 7, 8, 9, 10, 11, 12, 13, 14, 15, 16, 17, 18, 19, 20, 21, or 22, palmitoleic acid, vaccenic acid, erucic acid, oleic acid, alpha linolenic acid, gamma-linolenic acid, linoleic acid, gadoleic acid, arachidonic acid, docosahexaenoic acid (i.e., DHA), and eicosapentaenoic acid (i.e., EPA). The olefinic substrate may be solid (e.g., a fat) or liquid (e.g., an oil).

Preferred glycerides that may be used as the olefinic substrate are seed oils, or are compounds that derive from seed oils. Preferred seed oil sources include soybean oil, sunflower oil, canola oil, safflower oil, cottonseed oil, castor oil, rape seed oil, peanut oil, corn oil, olive oil, palm oil, sesame oil, grape seed oil, algae oil, mustard oil, tung oil, perilla oil, linseed oil, pumpkin oil, cucumber oil, poppyseed oil, flax seed oil, walnut oil, and sesame oil.

The olefinic substrate may be a compound or mixture of compounds that is derived from a glyceride using any one or combination of methods well known in the chemical arts. Such methods include saponification, esterification, hydrogenation, isomerization, oxidation, and reduction. For example, the olefinic substrate may the carboxylic acid or mixture of carboxylic acids that result from the saponification of a monoacylglycerol, diacylglycerol, triacylglycerol, or mixture thereof. In a preferred embodiment, the olefinic substrate is a fatty acid methyl ester (FAME), i.e., the methyl ester of a carboxylic acid that is derived from a glyceride. Sunflower FAME, safflower FAME, soy FAME (i.e., methyl soyate), algal FAME, and canola FAME are examples of such olefinic substrates. In addition, in some embodiments the olefinic substrates include seed oil-derived compounds such as methyl oleate.

The cross-metathesis partner that is reacted with the at least one internal olefin may be any olefinic compound that is capable of undergoing a metathesis reaction with the olefinic substrate to generate a terminal alkene product. The cross metathesis partner comprises an alpha olefin, wherein one olefinic carbon is unsubstituted and the other olefinic carbon is substituted with one or two non-hydrogen substituents. The substituted olefinic carbon may therefore be mono-substituted or di-substituted. The cross-metathesis partner may comprise a plurality of alpha olefins. A mixture of alpha olefins may be used.

Examples of monosubstituted alpha-olefins that may be used for the cross-metathesis partner include 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene and larger alpha olefins, 2-propenol, 3-butenol, 4-pentenol, 5-hexenol, 6-heptenol, 7-octenol, 8-nonenol, 9-decenol, 10-undecenol, 11-dodecenol, 12-tridecenol, 13-tetradecenol, 14-pentadecenol, 15-hexadecenol, 16-heptadecenol, 17-octadecenol, 18-nonadecenol, 19-eicosenol and larger alpha alkenols, 2-propenyl acetate, 3-butenyl acetate, 4-pentenyl acetate, 5-hexenyl acetate, 6-heptenyl acetate, 7-octenyl acetate, 8-nonenyl acetate, 9-decenyl acetate, 10-undecenyl acetate, 11-dodecenyl acetate, 12-tridecenyl acetate, 13-tetradecenyl acetate, 14-pentadecenyl acetate, 15-hexadecenyl acetate, 16-heptadecenyl acetate, 17-octadecenyl acetate, 18-nonadecenyl acetate, 19-eicosenyl acetate and larger alpha-alkenyl acetates, 2-propenyl chloride, 3-butenyl chloride, 4-pentenyl chloride, 5-hexenyl chloride, 6-heptenyl chloride, 7-octenyl chloride, 8-nonenyl chloride, 9-decenyl chloride, 10-undecenyl chloride, 11-dodecenyl chloride, 12-tridecenyl chloride, 13-tetradecenyl chloride, 14-pentadecenyl chloride, 15-hexadecenyl chloride, 16-heptadecenyl chloride, 17-octadecenyl chloride, 18-nonadecenyl chloride, 19-eicosenyl chloride and larger alpha-alkenyl chlorides, bromides, and iodides, allyl cyclohexane, allyl cyclopentane, and the like.

Examples of disubstituted alpha-olefins that may be used for the cross-metathesis partner include isobutylene, 2-methylbut-1-ene, 2-methylpent-1-ene, 2-methylhex-1-ene, 2-methylhept-1-ene, 2-methyloct-1-ene, and the like.

The components of the reactions of the present disclosure may be combined in any order, and it will be appreciated that the order of combining the reactants may be adjusted as needed. For example, the olefinic substrate may be added to the cross-metathesis partner, followed by addition of the catalyst. Alternatively, the olefinic substrate and cross-metathesis partner may be added to the catalyst. When one of the reactants is a gas, it may be necessary to add the catalyst to the liquid or solid reactant before introducing the gaseous reactant.

The catalyst may be added to the reaction either as a solid, dissolved in one of the reactants, or dissolved in a solvent. The catalyst may be added in any quantity and manner effective for the intended results of the reaction. For example, predetermined amounts of catalyst can be sequentially added to the reaction mixture at predetermined time intervals.

The reactions of the present disclosure may be carried out in a solvent, and any solvent that is inert towards cross metathesis may be employed. Generally, solvents that may be used in the cross-metathesis reactions include organic, protic, or aqueous solvents, such as aromatic hydrocarbons, chlorinated hydrocarbons, ethers, aliphatic hydrocarbons, alcohols, Water, or mixtures thereof. Example solvents include benzene, toluene, p-xylene, methylene chloride, 1,2-dichloroethane, dichlorobenzene, chlorobenzene, tetrahydrofuran, diethylether, pentane, methanol, ethanol, water, or mixtures thereof. In certain embodiments, the reactions of the present disclosure are carried out neat, i.e., without the use of a solvent.

The temperature at which a cross metathesis reaction according to the present disclosure is conducted can be adjusted as needed, and may be at least about −78° C., about −40° C., about −10° C., about 0° C., about 10° C., about 20° C., about 25° C., about 35° C., about 50° C., about 100° C., or about 150° C.

The product(s) of the reactions according to the present disclosure can be purified by any of the methods commonly known and used in the art, including, for example, distillation and crystallization. Any excess of alpha-olefin (which is a terminal olefin or alkene with a chemical formula RR'C=CH$_2$, where R and R' are each independently H, alkyl, aryl, heteroalkyl, heteroaryl, alkoxy, alkenyl, alkynyl, or acyl) after the reaction is completed can be separated from the final reaction mixture and recycled. Furthermore, any internal olefins present in the final reaction mixture can be separated, optionally purified, and recycled or used in a different reaction. A mixture of terminal olefins and internal olefins (e.g., terminally unsaturated esters and internally unsaturated esters) produced by the processes described herein can be separated from the final reaction mixture and used in a subsequent reaction. For example, such products may be used in another metathesis process (e.g., a metathesis process wherein the terminally unsaturated esters and internally unsaturated esters are converted into diesters).

In certain embodiments, the invention relates to any one of the aforementioned methods, wherein the alpha olefin and the olefinic substrate are part of the same molecule. In certain embodiments, the alpha olefin and the internal olefin are separated by a covalent linker.

In certain embodiments, the catalyst is present in an amount ranging from about 1 ppm to about 50 ppm relative to the number of olefinic substrate double bonds. Generally, preferred catalyst amounts of about 1 to 10 ppm can be used.

According to an aspect of the invention, the reaction is carried out by contacting, under an inert atmosphere and in the presence of a ruthenium alkylidene metathesis catalyst, an olefinic substrate comprising at least one internal olefin with a cross-metathesis partner comprising an alpha olefinic reactant, under reaction conditions effective to allow cross-metathesis to occur.

According to another aspect of the invention, the reaction is carried out by contacting, in an oxygen-containing atmosphere and in the presence of a ruthenium alkylidene metathesis catalyst, an olefinic substrate comprising at least one internal olefin with a cross metathesis partner comprising an alpha olefinic reactant, under reaction conditions effective to allow cross metathesis to occur.

In certain embodiments, the reaction is carried out by contacting, in the presence of a ruthenium alkylidene metathesis catalyst, an olefinic substrate comprising a mixture of monoglycerides, diglycerides, and triglycerides, with a cross metathesis partner comprising an alpha olefinic reactant, under reaction conditions effective to allow cross-metathesis to occur.

According to another aspect of the invention, the reaction is carried out by contacting, under an inert atmosphere and in the presence of a ruthenium alkylidene metathesis catalyst, an olefinic substrate comprising at least one internal olefin with a cross metathesis partner comprising an alpha olefinic reactant, under reaction conditions effective to allow cross-metathesis to occur, wherein the moles of the olefinic substrate is approximately equal to 1 to 9 times the moles of the cross metathesis partner.

According to a further aspect, the reaction is carried out by contacting, in the presence of a ruthenium alkylidene metathesis catalyst, an olefinic substrate comprising at least one internal olefin with a cross metathesis partner comprising an alpha olefinic reactant, with a cross metathesis partner comprising an alpha olefinic reactant, under reaction conditions effective and to allow cross-metathesis to occur, wherein the internal olefin has a molecular weight (MW) of at least 250 g/mol, or has at least 7 carbon atoms. Preferably the internal olefin has a molecular weight from about 300 g/mol to about 1000 g/mol, or has from 20 to 60 carbons. Such high-MW internal olefin substrates can include readily available, inexpensive olefins or mixtures of olefins such as unsaturated or polyunsaturated triacylglycerides obtained from plant or animal oils, high-boiling petrochemical fractions, or elastomeric or other unsaturated polymers (e.g., polybutadienes or polyisoprenes). Mixtures of such high-MW olefins are typically difficult to separate due to their high boiling points and relatively similar boiling point ranges. They can also be difficult to purify because of the high temperatures required for distillation. Cross-metathesis of these high-MW substrates can be efficiently performed with alpha olefins, especially lower alpha olefins, to produce lower-MW products that can be more easily separated or purified. In preferred embodiments, the high-MW internal olefin substrate is a triacylglyceride or a mixture of triacylglycerides. Such compounds could be saponified to mixtures of lower MW FAMEs, although such mixtures are still difficult to separate. If mixed FAMEs are used as substrates for cross metathesis, very complex mixtures of products are obtained. However, cross-metathesis of triacylglycerides can be efficiently performed with alpha olefins. By proper selection of the alpha-olefin, in particularly using lower alpha olefins such as propene or butene, relatively low-MW hydrocarbon olefins are produced that can be easily separated from the metathesized triacylglyceride fragment. In a subsequent step, the remaining triacylglyceride fragment can be saponified to yield unsaturated carboxylate compounds.

In a preferred embodiment, the turnover number (TON), defined as the moles of terminal olefin product formed per mol of catalyst, of the process is at least 50,000, preferably at least 100,000, preferably at least 500,000.

In a preferred embodiment, the yield, defined as the moles of terminal olefin product formed per mol of olefinic substrate, is 30% or more, preferably 40% or more, preferably 45% or more, preferably 50% or more, preferably 55% or more, preferably 60% or more.

Exemplary Products

In certain embodiments, the invention relates to an olefin product produced by any one of the methods described herein.

DEFINITIONS

Unless otherwise indicated, the disclosure is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an alpha olefin" includes a single alpha olefin as well as a combination or mixture of two or more alpha olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. If not otherwise indicated, the terms "alkyl" and "lower alkyl" include linear, branched, cyclic, unsubstituted, or substituted alkyl and lower alkyl, respectively.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like.

The term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "heteroaralkyl," as used herein, refers to an alkyl group substituted with a heteroaryl group.

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The term "heteroaryl" also includes polycyclic ring systems having two or more cyclic rings in which two or more carbons are common to two adjoining rings wherein at least one of the rings is heteroaromatic. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroatom," as used herein, means an atom of any element other than carbon or hydrogen. Preferred heteroatoms are nitrogen, oxygen, and sulfur, most preferably oxygen and nitrogen.

The term "heterocyclyl" refers to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "hydrocarbyl," as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

EXEMPLIFICATION

The invention now being generally described, it will be more readily understood by reference to the following examples which are included merely for purposes of illustration of certain aspects and embodiments of the present invention, and are not intended to limit the invention.

Example 1

Ru9-Ru11 (Scheme 2) were synthesized in moderate to excellent yields (20-90%). These catalysts all displayed unprecedented activity in the ethenolysis of methyl oleate (Scheme 3). Specifically, catalysts Ru9 and Ru10, provided TONs>100,000 at only 3 ppm catalyst loading under optimized reaction conditions (Table 1). High purity ethylene (>99%) was used in this experiment; previous studies had utilized lower quality ethylene (>95%), containing significant amounts (>5 ppm) of unsaturated impurities including acetylene. These impurities may lead to premature catalyst death at lower catalyst loadings.

The backbone substitution of the CAAC ligands was varied. The gem-dimethyl groups of Ru10 may be replaced with only a slight loss in activity (as in Ru13). This small change in the steric environment a to the carbene carbon afforded access to catalysts bearing previously unaccessible N-aryl substituents, such as Ru14 and Ru15 in good conversion (60-80%). Although these catalysts performed well, TONs were still not as high as those observed for Ru9, Ru10, and Ru13. Too much substitution at the α-carbon (cyclohexyl, adamantyl) appeared to impede reactivity (as in Ru16 and Ru17); this was especially prevalent in catalysts bearing bulky N-ortho substituents (Ru12).

Replacement of one of the gem-dimethyl substituents alpha to the carbene carbon with an aromatic ring, as in catalysts Ru18-Ru21, also had a profound effect. The trend for TON for various N-aryl substituents was similar to that found for the other catalyst systems (Ru7-Ru17).

Figure 2:
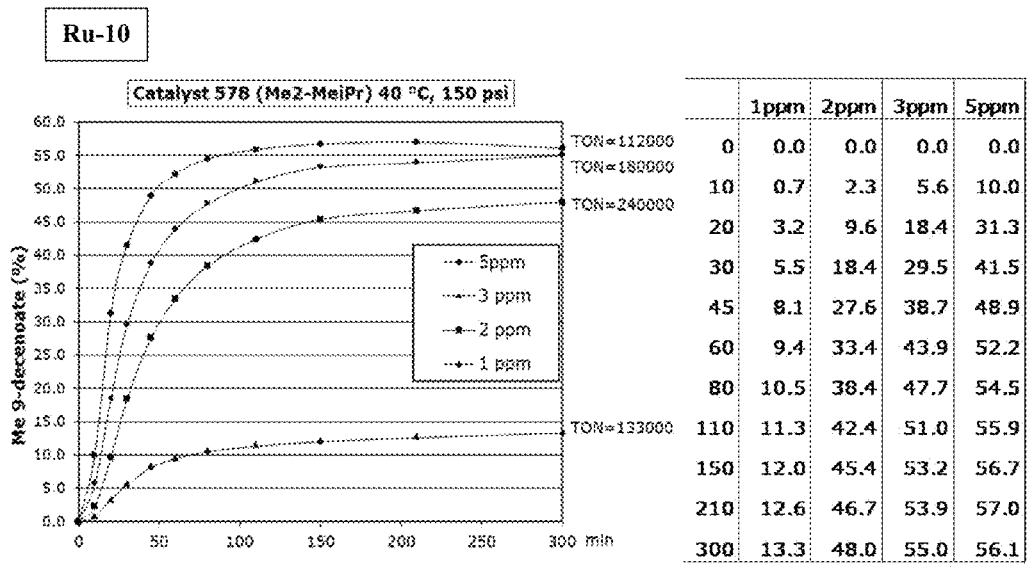
FIG. 2 depicts the evolution of conversion as a function of reaction time at varying catalyst loading of catalyst Ru-10 (FIG. 2a), varying pressures and temperatures (FIG. 2b), and varying catalysts (FIG. 2c).
Figure 2:
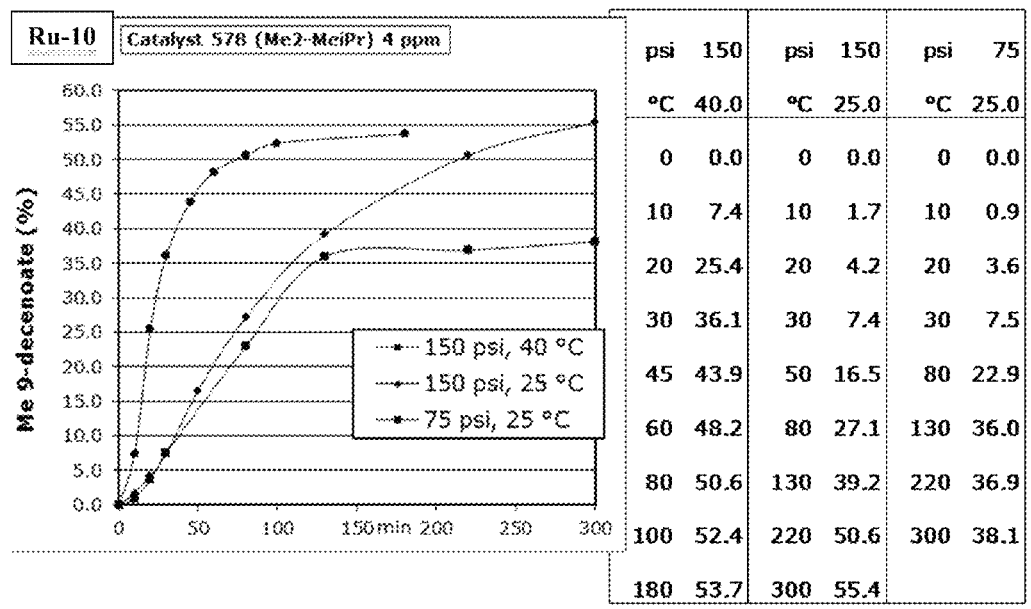

See FIG. 2.

Scheme 2

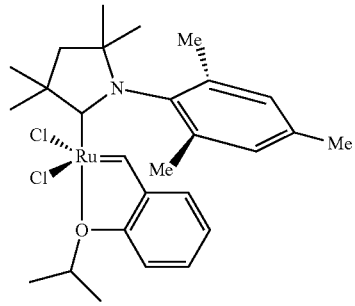

Ru-7

Ru-8
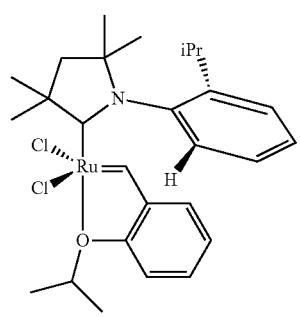
Ru-9
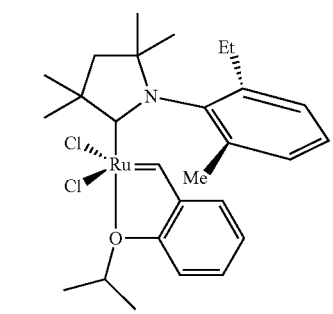
Ru-10
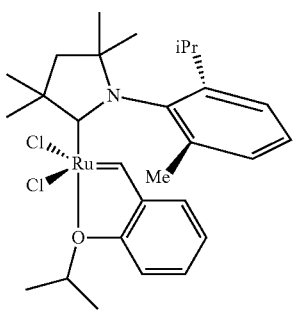
Ru-11
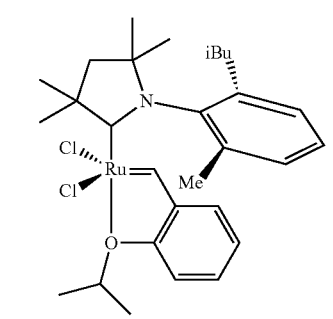
Ru-12
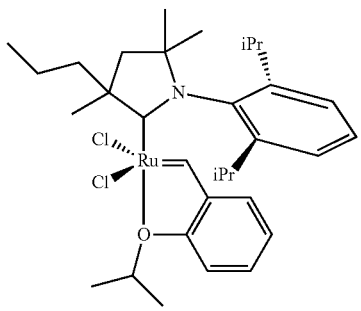
Ru-13
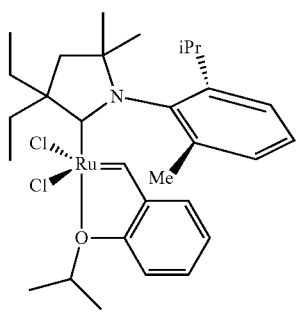
Ru-14
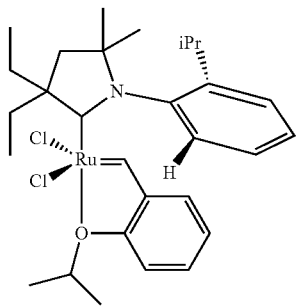
Ru-15
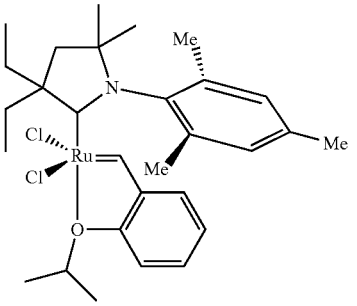
Ru-16
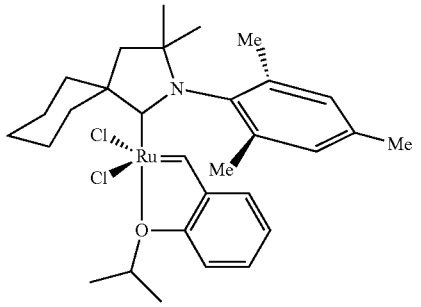
Ru-17
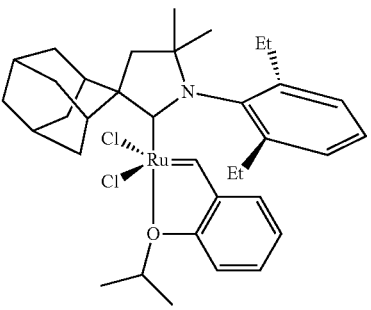

-continued

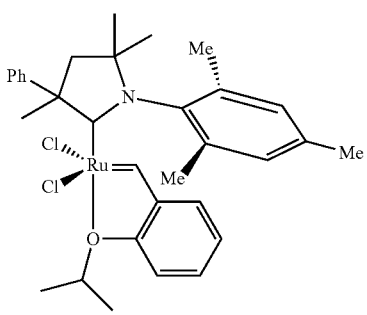
Ru-18

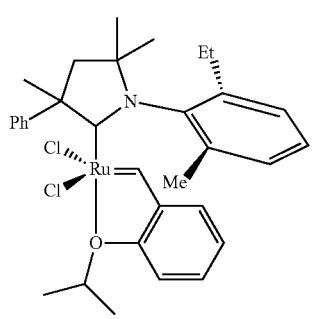
Ru-19

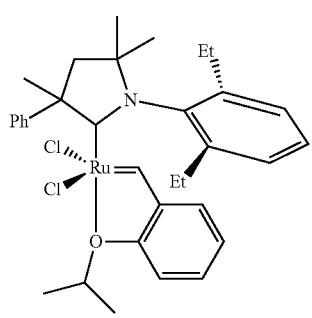
Ru-20

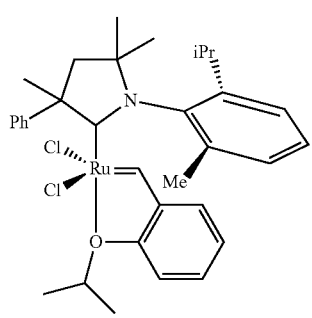
Ru-21

Scheme 3

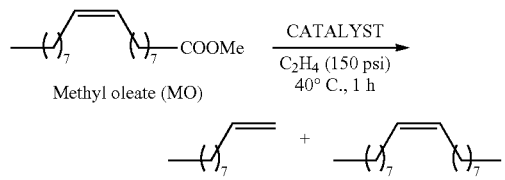
Methyl oleate (MO)

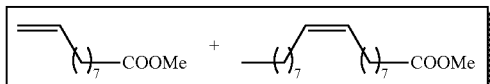

TABLE 1

| CATALYST | LOADING (PPM)[a] | TON[b] | Conversion (%)[c] | SELECTIVITY (%)[d] |
|---|---|---|---|---|
| Ru4 | 3 | 125,000 | 42 | 88 |
| Ru6 | 3 | 60,000 | 19 | 97 |
| Ru9 | 3 | 110,000 | 37 | 86 |
| Ru10 | 2 | 240,000 | 51 | 92 |
|  | 3 | 180,000 | 59 | 92 |
| Ru11 | 3 | 50,000 | 17 | 94 |
| Ru12 | 3 | ND | <10 | N/A |
| Ru13 | 3 | 130,000 | 42 | 92 |
| Ru14 | 3 | 45,000 | 22 | 63 |
| Ru15 | 3 | 74,000 | 26 | 86 |
| Ru16 | 3 | 48,000 | 19 | 78 |
| Ru17 | 3 | ND | <10 | N/A |
| Ru18 | 3 | 114,000 | 41 | 83 |
| Ru19 | 3 | 129,000 | 46 | 85 |
| Ru20 | 3 | 142,000 | 48 | 88 |
| Ru21 | 3 | 175,000 | 56 | 94 |

[a] loading = (moles catalyst/starting moles MO), reactions were generally conducted using 15 g MO;
[b] TON = (½ * moles ethenolysis products/starting moles of MO) * (1/loading);
[c] Conversion = 100 * (½ * moles ethenolysis products + moles self-metathesis products)/(starting moles of MO), determined via GC (Agilent technologies, HP1 column) using dodecane as an internal standard;
[d] Selectivity = 100 * (moles ethenolysis products)/(moles ethenolysis products + 2 * self-metathesis products)

While not wishing to be bound by any particular theory, the exceptional activity displayed by the most active catalysts is hypothesized to be a result of a balance between catalyst initiation and decomposition, both of which increase with decreasing substitution about the CAAC carbene carbon. Asymmetrical ortho-substitution about the N-aryl ring of the CAAC ligand appears to be beneficial in achieving this desired increase in propensity towards substrate turnover in lieu of catalyst decomposition.

Example 2

Initiation rates were measured by reacting catalysts with n-butylvinylether. As a comparison, the initiation rate constants of known catalysts are also included (i.e., Ru4 and SD-Hoveyda (i.e., the second-generation Grubbs-Hoveyda catalyst)). As depicted in Table 2, the less bulky catalysts initiating much faster. The mono-substituted isopropyl derivative Ru6 initiates especially rapidly, and in fact could not be monitored at 60° C. for direct comparison to the others because the reaction was complete by the time the first data point was obtained at 90 s. It is interesting to note that the MIPP catalyst Ru10 barely reacts until about 50° C.

TABLE 2

| CATALYST | Catalyst #, FIG. 1 | TEMP (° C.) | INITIATION RATE CONSTANT, $10^{-3}$ s$^{-1}$ |
|---|---|---|---|
| Ru21 | 1 | 60 | 0.23 ± 0.02 |
| Ru11 | 2 | 60 | 0.24 ± 0.02 |
| Ru10 | 3 | 60 | 0.29 ± 0.03 |
| Ru9 | 5 | 60 | 3.2 ± 0.3 |
| Ru8 | 6 | 60 | [b] |
| Ru8 | 6 | 30 | 1.1 ± 0.1 |
| Ru4 | 4 | 60 | 1.3 ± 0.1 |
| SD-Hov |  | 30 | 7.2 ± 0.2 |

[a] Initiation rate constants were determined by measuring the decrease in the benzylidene resonance using $^1$H NMR spectroscopy following addition of BVE (measurements conducted in triplicate). Conditions were catalyst (0.003 mmol) and BVE (0.09 mmol) in C$_6$D$_6$ (0.6 mL) at given temperature.
[b] Complete initiation had occurred within 90 s.

Example 3

The steady-state cross-metathesis (CM) of 1-hexene (sealed in an NMR tube) (Scheme 4)

Scheme 4

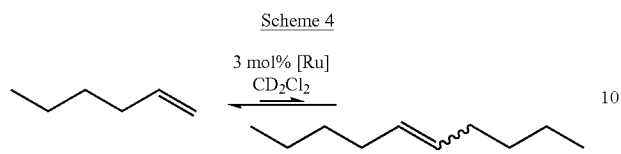

was examined to see if a correlation could be made to the selectivity noted in the ethenolysis of methyl oleate. In general, the CAACs seem to exhibit similar selectivity to previously reported N-alkyl N-aryl catalysts (which range from 10-20% conversion). It is interesting that except for the disubstituted N-aryl derivatives, N-aryl substitution does not appear to influence the preference of the catalysts for terminal olefins, however phenyl substitution on the backbone as in 1 (i.e., Ru21) decreases the selectivity somewhat. Also, the monounsubstituted derivative 6 (i.e., Ru8) did not reach a steady state after 6 hours.

See FIG. 1.

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound, wherein the compound is
(A) a compound of Formula I:

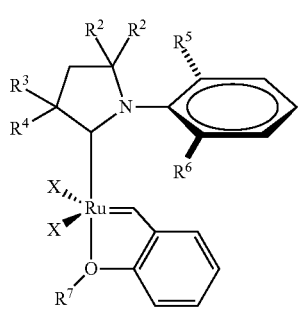

Formula I wherein, independently for each occurrence,
X is, independently for each occurrence, alkoxy or halo;
$R^2$ is, independently for each occurrence, alkyl;
$R^3$ is alkyl;
$R^4$ is alkyl, aryl, heteroaryl, aralkyl, or heteroaralkyl;
or $R^3$ and $R^4$, taken together with the carbon atom to which they are attached, form a five-, six-, or ten-membered cycloalkyl or heterocyclyl ring;
$R^5$ is alkyl;
$R^6$ is H or alkyl, provided that (i) $R^5$ and $R^6$ are not the same, and (ii) $R^6$ has fewer atoms than $R^5$; and
$R^7$ is alkyl;

(B) a compound of Formula II:

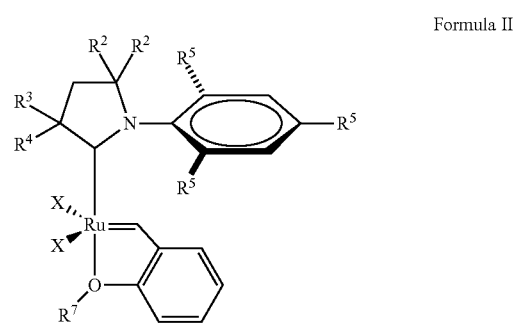

Formula II wherein, independently for each occurrence,
X is, independently for each occurrence, alkoxy or halo;
$R^2$ is, independently for each occurrence, alkyl;
$R^3$ is alkyl;
$R^4$ is alkyl, aryl, heteroaryl, aralkyl, or heteroaralkyl;
or $R^3$ and $R^4$, taken together with the carbon atom to which they are attached, form a five-, six-, or ten-membered cycloalkyl or heterocyclyl ring;
$R^5$ is, independently for each occurrence, alkyl; and
$R^7$ is alkyl;

(C) a compound of Formula III:

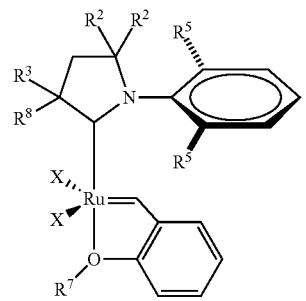

Formula III wherein, independently for each occurrence,
X is, independently for each occurrence, alkoxy or halo;
$R^2$ is alkyl;
$R^3$ is alkyl;
$R^5$ is, independently for each occurrence, methyl or ethyl;
$R^7$ is alkyl; and
$R^8$ is aryl or heteroaryl; or (D) a compound of Formula IV:

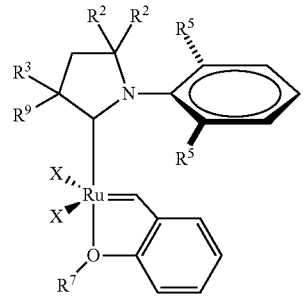

Formula IV wherein, independently for each occurrence,
X is, independently for each occurrence, alkoxy or halo;
$R^2$ is alkyl;

$R^3$ is alkyl;

$R^5$ is, independently for each occurrence, alkyl;

$R^7$ is alkyl; and $R^9$ is $C_2$-$C_6$ alkyl;

or $R^3$ and $R^9$, taken together with the carbon atom to which they are attached, form a five-, or ten-membered cycloalkyl or heterocyclyl ring.

2. The compound of claim 1, wherein X is chloro.

3. The compound of claim 1, wherein $R^2$ is methyl.

4. The compound of claim 1, wherein $R^3$ is ethyl or methyl.

5. The compound of claim 1, wherein the compound is a compound of Formula I or a compound of Formula II; and $R^4$ is ethyl or methyl.

6. The compound of claim 1, wherein the compound is a compound of Formula I or a compound of Formula II; and $R^4$ is phenyl.

7. The compound of claim 1, wherein the compound is a compound of Formula I or a compound of Formula II; and $R^3$ and $R^4$, taken together with the carbon atom to which they are attached, form a cyclohexyl ring.

8. The compound of claim 1, wherein the compound is a compound of Formula I, Formula II, or Formula IV, and $R^5$ is methyl, ethyl, iso-propyl, or tert-butyl.

9. The compound of claim 1, wherein the compound is a compound of Formula I; and $R^6$ is H or methyl.

10. The compound of claim 1, wherein $R^7$ is iso-propyl.

11. The compound of claim 1, wherein the compound is a compound of Formula III; and $R^8$ is phenyl.

12. The compound of claim 1, wherein the compound is a compound of Formula IV; and $R^9$ is n-propyl.

13. A compound selected from:

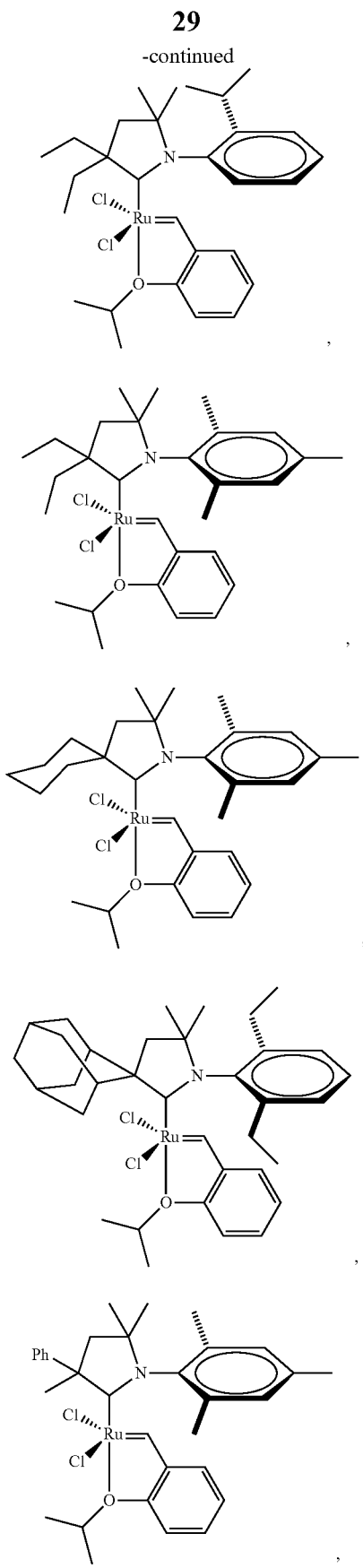

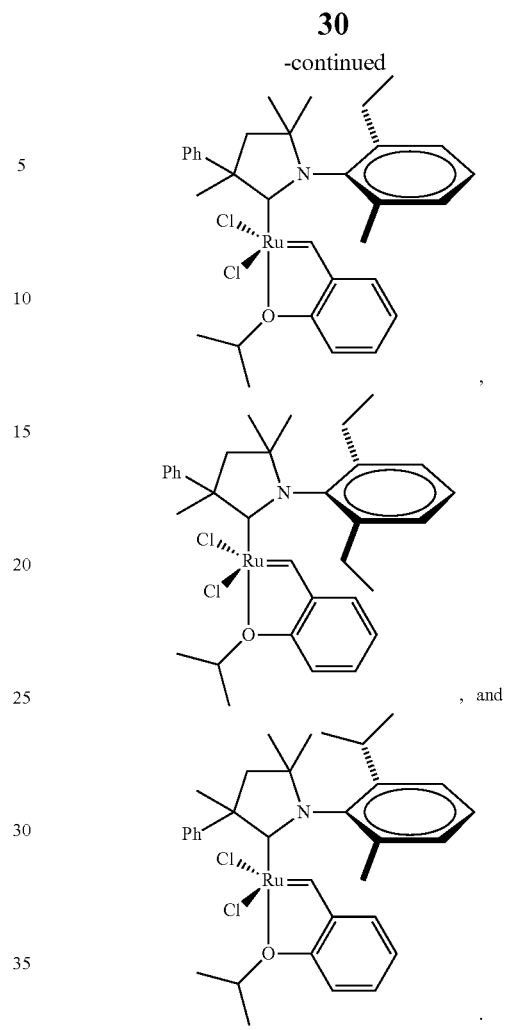

, and

14. A method of producing an olefin product comprising:
providing an olefinic substrate;
providing an alpha olefin;
contacting the olefinic substrate with the alpha olefin in the presence of a compound of claim 1 under reaction conditions effective to allow a metathesis reaction to occur, thereby producing the olefin product.

15. The method of claim 14, wherein the olefin product is a terminal olefin product.

16. The method of claim 14, wherein the olefinic substrate comprises at least one internal olefin.

17. The method of claim 14, wherein the olefinic substrate is a cyclic olefin.

18. The method of claim 14, wherein the olefinic substrate is an ester of glycerol.

19. The method of claim 14, wherein the olefinic substrate is a seed oil.

20. The method of claim 19, wherein the seed oil is selected from: soybean oil, sunflower oil, canola oil, safflower oil, cottonseed oil, castor oil, rape seed oil, peanut oil, corn oil, olive oil, palm oil, sesame oil, grape seed oil, algae oil, mustard oil, tung oil, perilla oil, linseed oil, pumpkin oil, cucumber oil, poppyseed oil, flax seed oil, walnut oil, and sesame oil.

21. The method of claim 14, wherein the turnover number is at least 50,000.

* * * * *